US00PP29037P3

(12) United States Plant Patent
Grazzini

(10) Patent No.: US PP29,037 P3
(45) Date of Patent: Feb. 27, 2018

(54) ***SUTERA* PLANT NAMED 'G13340'**

(50) Latin Name: *Sutera cordata*
Varietal Denomination: G13340

(71) Applicant: Richard A. Grazzini, Bellefonte, PA (US)

(72) Inventor: Richard A. Grazzini, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 27 days.

(21) Appl. No.: 14/999,694

(22) Filed: Jun. 16, 2016

(65) Prior Publication Data

US 2017/0367247 P1 Dec. 21, 2017

(51) Int. Cl.
*A01H 5/02* (2006.01)

(52) U.S. Cl.
USPC ..... Plt./485

(58) Field of Classification Search
USPC ..... Plt./485
See application file for complete search history.

(56) References Cited

PUBLICATIONS

UPOV hit on *Sutera* plant named 'G13340', CA PBR 16-8896, application filed Mar. 30, 2016.*

* cited by examiner

*Primary Examiner* — Anne M Grunberg
(74) *Attorney, Agent, or Firm* — C. A. Whealy

(57) ABSTRACT

A new and distinct cultivar of *Sutera* plant named 'G13340', characterized by its cascading to trailing plant habit; moderately vigorous growth habit; freely branching habit; early and freely flowering habit; large medium blue-colored flowers; and long flowering season.

1 Drawing Sheet

Botanical designation: *Sutera cordata.*
Cultivar denomination: 'G13340'.

BACKGROUND OF THE INVENTION

The present invention relates to a new and distinct cultivar of *Sutera* plant, botanically known as *Sutera cordata* and hereinafter referred to by the name 'G13340'.

The new *Sutera* plant is a product of a planned breeding program conducted by the Inventor in Bellefonte, Pa. The objective of the breeding program is to create new cascading *Sutera* plants with numerous large blue-colored flowers and long flowering period.

The new *Sutera* plant originated from a cross-pollination conducted by the Inventor in October, 2012 in Bellefonte, Pa. of a proprietary selection of *Sutera cordata* identified as code number 23636-2, not patented, as the female, or seed, parent with a proprietary selection of *Sutera cordata* identified as code number 23639-5, not patented, as the male, or pollen, parent. The new *Sutera* plant was discovered and selected by the Inventor as a flowering plant from within the progeny of the stated cross-pollination in a controlled greenhouse environment in Bellefonte, Pa. in September, 2013.

Asexual reproduction of the new *Sutera* plant by terminal cuttings in a controlled greenhouse environment in Bellefonte, Pa. since November, 2013, has shown that the unique features of this new *Sutera* plant are stable and reproduced true to type in successive generations.

SUMMARY OF THE INVENTION

Plants of the new *Sutera* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G13340'. These characteristics in combination distinguish 'G13340' as a new and distinct *Sutera* plant:

1. Cascading to trailing plant habit.
2. Moderately vigorous growth habit.
3. Freely branching habit.
4. Early and freely flowering habit.
5. Large medium blue-colored flowers.
6. Long flowering season.

Plants of the new *Sutera* can be compared to plants of the female parent selection. Plants of the new *Sutera* differ primarily from plants of the female parent selection in the following characteristics:

1. Plants of the new *Sutera* have larger flowers than plants of the female parent selection.
2. Plants of the new *Sutera* flower for a longer period of time than plants of the female parent selection.

Plants of the new *Sutera* can be compared to plants of the male parent selection. Plants of the new *Sutera* differ primarily from plants of the male parent selection in the following characteristics:

1. Plants of the new *Sutera* have larger flowers than plants of the male parent selection.
2. Flowers of plants of the new *Sutera* are darker blue in color than flowers of plants of the male parent selection.
3. Plants of the new *Sutera* flower for a longer period of time than plants of the male parent selection.

Plants of the new *Sutera* can be compared to plants of the *Sutera cordata* 'Wesbablue', disclosed in U.S. Plant Pat. No. 14,192. In side-by-side comparisons conducted in Bellefonte, Pa., plants of the new *Sutera* differ primarily from plants of 'Wesbablue' in the following characteristics:

1. Plants of the new *Sutera* are more cascading and trailing than plants of 'Wesbablue'.
2. Plants of the new *Sutera* have longer internodes than plants of 'Wesbablue'.
3. Plants of the new *Sutera* have darker green-colored leaves than plants of 'Wesbablue'.
4. Plants of the new *Sutera* have larger flowers than plants of 'Wesbablue'.
5. Plants of the new *Sutera* and 'Wesbablue' differ in flower color as plants of 'Wesbablue' have violet blue-colored flowers.
6. Plants of the new *Sutera* flower for a longer period of time than plants of 'Wesbablue'.

Plants of the new *Sutera* can be compared to plants of the *Sutera diffusa* 'Sutcabl', disclosed in U.S. Plant Pat. No. 17,234. In side-by-side comparisons conducted in Bellefonte, Pa., plants of the new *Sutera* differ primarily from plants of 'Sutcabl' in the following characteristics:

1. Plants of the new *Sutera* are more vigorous than and not as compact as plants of 'Sutcabl'.
2. Plants of the new *Sutera* have longer internodes than plants of 'Sutcabl'.
3. Plants of the new *Sutera* have darker green-colored leaves than plants of 'Sutcabl'.
4. Plants of the new *Sutera* have larger flowers than plants of 'Sutcabl'.
5. Plants of the new *Sutera* and 'Sutcabl' differ in flower color as plants of 'Sutcabl' have dark blue-colored flowers.
6. Plants of the new *Sutera* flower for a longer period of time than plants of 'Sutcabl'.

BRIEF DESCRIPTION OF THE PHOTOGRAPHS

The accompanying colored photographs illustrate the overall appearance of the new *Sutera* plant showing the colors as true as it is reasonably possible to obtain in colored reproductions of this type. Colors in the photographs may differ slightly from the color values cited in the detailed botanical description which accurately describe the colors of the new *Sutera* plant.

The photograph at the bottom of the sheet is a side perspective view of a typical flowering plant of 'G13340' grown in a container.

The photograph at the top of the sheet is a close-up view of a typical flowering plant of 'G13340'.

DETAILED BOTANICAL DESCRIPTION

The aforementioned photographs and following observations and measurements describe plants grown during the autumn in 10-cm containers in an acrylic-covered greenhouse in Carleton, Mich. and under cultural practices typical of commercial *Sutera* production. During the production of the plants, day and night temperatures ranged from 18° C. to 31° C. Plants were pinched one time and were five weeks from planting rooted cuttings when the photographs and description were taken. In the following description, color references are made to The Royal Horticultural Society Colour Chart, 2007 Edition, except where general terms of ordinary dictionary significance are used.

Botanical classification: *Sutera cordata* 'G13340'.

Parentage:

*Female, or seed, parent*.—Proprietary selection of *Sutera cordata* identified as code number 23636-2, not patented.

*Male or pollen parent*.—Proprietary selection of *Sutera cordata* identified as code number 23639-5, not patented.

Propagation:

*Type*.—By terminal cuttings.

*Time to initiate roots, summer and winter*.—About seven to ten days at soil temperatures ranging from about 21° C. to 22° C.

*Time to produce a rooted young plant, summer*.—About three to four weeks at soil temperatures ranging from about 21° C. to 22° C.

*Time to produce a rooted young plant, winter*.—About four to five weeks at soil temperatures ranging from about 21° C. to 22° C.

*Root description*.—Medium in thickness, fibrous; creamy white in color.

*Rooting habit*.—Freely branching; medium density.

Plant description:

*Plant and growth habit*.—Cascading to trailing plant habit; moderately vigorous growth habit; moderate growth rate.

*Plant height, soil level to top of foliar plane*.—About 7.5 cm.

*Plant height, soil level to top of floral plane*.—About 8.5 cm.

*Plant diameter (area of spread)*.—About 24 cm.

Lateral branch description:

*Branching habit*.—Freely branching habit; when pinched, about three to four primary lateral branches each with up to six secondary lateral branches develop per plant.

*Length*.—About 14 cm.

*Diameter*.—About 2 mm.

*Internode length*.—About 1.5 cm.

*Strength*.—Moderately strong to strong.

*Aspect*.—Horizontally spreading to trailing.

*Texture and luster*.—Slightly pubescent; matte.

*Color, developing and fully developed*.—Close to 144A.

Leaf description:

*Arrangement*.—Before flowering, alternate; after flowering, opposite, simple.

*Length*.—About 1.8 cm.

*Width*.—About 1.7 cm.

*Shape*.—Broadly elliptic to rounded deltoid.

*Apex*.—Acute.

*Base*.—Attenuate.

*Margin*.—Proximally, entire; distally, serrulate.

*Texture and luster, upper and lower surfaces*.—Scattered pubescent; slightly glossy.

*Venation pattern*.—Pinnate, reticulate.

*Color*.—Developing leaves, upper surface: Close to N137B. Developing leaves, lower surface: Close to 147B. Fully expanded leaves, upper surface: Close to N137A; venation, close to N137A. Fully expanded leaves, lower surface: Close to N137D; venation, close to N137B.

*Petioles*.—Length: About 3.5 mm. Diameter: About 1 mm. Strength: Moderately strong. Texture and luster, upper and lower surfaces: Sparsely pubescent;

slightly glossy. Color, upper surface: Close to 137A. Color, lower surface: Close to 146B.

Flower description:

*Flower arrangement*.—Large single salverform flowers; freely flowering habit with potentially about 100 flower buds and open flowers per plant at one time; flowers face mostly upright then turning outwardly.

*Fragrance*.—None detected.

*Flowering habit*.—Early flowering habit, plants begin flowering about five weeks after planting; long flowering season, plants flower continuously from July to September in Michigan.

*Flower longevity*.—Flowers last about five days on the plant; flowers persistent.

*Flower diameter*.—About 1.7 cm.

*Flower length* (*height*).—About 1.8 cm.

*Throat diameter*.—About 4 mm.

*Tube length*.—About 1.1 cm.

*Tube diameter, mid-section*.—About 3 mm.

*Flower buds*.—Length: About 8 mm. Diameter: About 4 mm. Shape: Obovate. Texture and luster: Smooth; matte. Color: Close to 92D.

*Petals*.—Quantity and arrangement: Five per flower in a single whorl; fused at the base. Lobe length: About 7 mm. Lobe width: About 7 mm. Lobe shape: Orbicular. Lobe apex: Obtuse, rounded. Lobe margin: Entire. Texture and luster, petal lobes, upper and lower surfaces: Smooth, glabrous; matte. Texture, throat and tube: Pubescent, hairs minute. Color: Petal lobes, when opening, upper surface: Close to 92B to 92C. Petal lobes, when opening, lower surface: Close to 92D. Petal lobes, fully opened, upper surface: Close to 90C; venation, close to 90C; color shifts slightly to N88B with development. Petal lobes, fully opened, lower surface: Close to 90D; venation, close to 90D; color does not change with development. Throat: Close to N163B; venation, close to N163B. Tube: Mid-section and towards the base, close to 164B; towards the apex, close to 159B; venation, close to 164B to 164C.

*Sepals*.—Quantity and arrangement: Five per flower in a single whorl; fused at the base; calyx, star-shaped. Length: About 6 mm. Width: About 1 mm. Shape: Lanceolate. Apex: Acute. Margin: Entire. Texture and luster, upper and lower surfaces: Pubescent, minute; matte. Color: When opening and fully opened, upper surface: Close to N137A. When opening and fully opened, lower surface: Close to N137B.

*Peduncles*.—Length: About 6 mm. Diameter: About 1 mm. Angle: About 45° from vertical. Strength: Moderately strong. Texture and luster: Pubescent, minute; matte. Color: Close to 137B.

*Reproductive organs*.—Androecium: Quantity of stamens per flower: About four. Filament length: About 6 mm. Filament color: Close to NN155D. Anther shape: Oval. Anther size: About 1.5 mm by 1 mm. Anther color: Close to 161A. Amount of pollen: Scarce. Pollen color: Close to 12B. Gynoecium: Quantity of pistils per flower: One. Pistil length: About 1.2 cm. Style length: About 8 mm. Style color: Close to 145B. Stigma shape: Lanceolate. Stigma color: Close to 144A. Ovary color: Close to 144A.

*Seeds & fruits*.—Seed and fruit production have not been observed on plants of the new *Sutera*.

Garden performance: Plants of the new *Sutera* have been observed to have good garden performance and to tolerate wind, rain and suitable for USDA Hardiness Zones 9 to 11.

Pathogen & pest tolerance: Plants of the new *Sutera* have not been observed to be tolerant to pathogens and pests common to *Sutera* plants.

It is claimed:

1. A new and distinct *Sutera* plant named 'G13340' as illustrated and described.

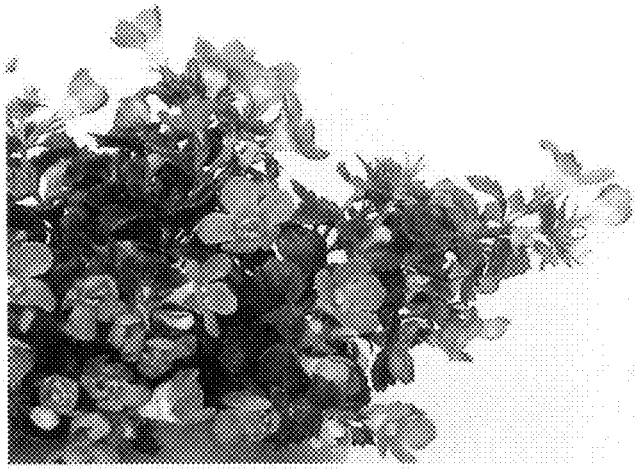
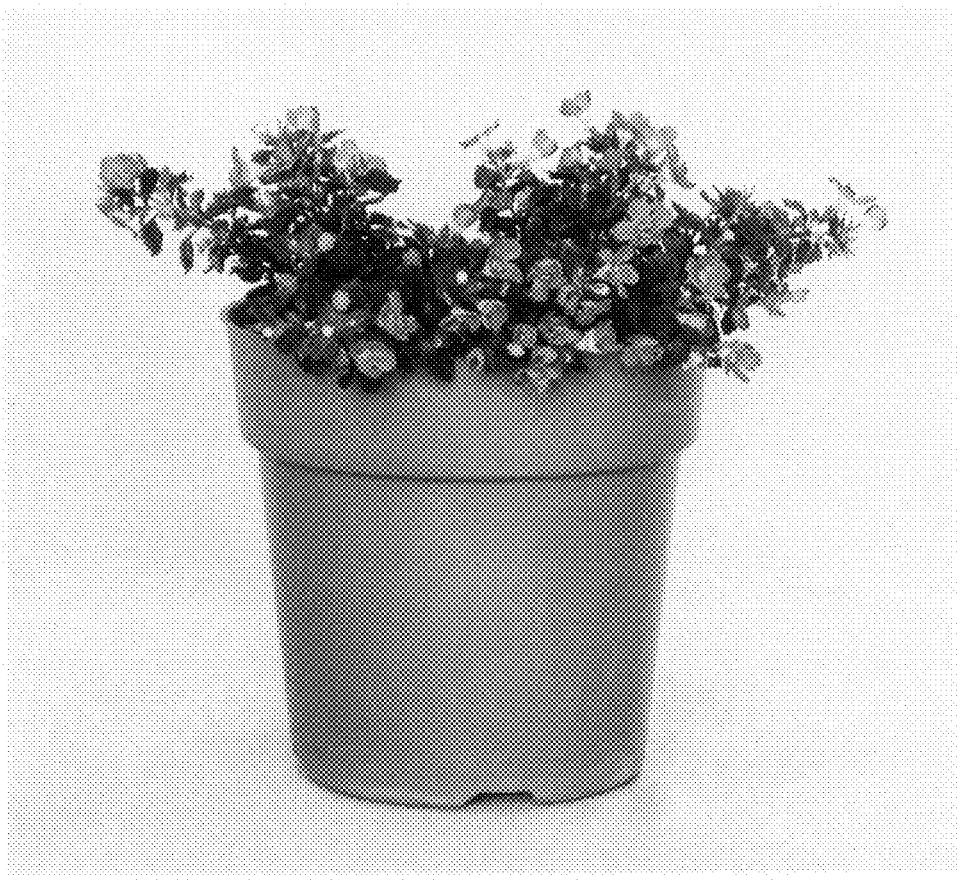

* * * * *